United States Patent [19]

Lohmann et al.

[11] Patent Number: 4,997,965
[45] Date of Patent: Mar. 5, 1991

[54] ENANTIOMERIC SILANES, MODIFIED PACKING MATERIAL, AND USE THEREOF

[75] Inventors: Dieter Lohmann; Richard Däppen, both of Münchenstein, Switzerland

[73] Assignee: Ciba-Geigy Corporation, Ardsley, N.Y.

[21] Appl. No.: 445,921

[22] Filed: Dec. 4, 1989

[30] Foreign Application Priority Data

Dec. 20, 1988 [CH] Switzerland .................... 4762/88

[51] Int. Cl.⁵ ..................... C07F 7/10; C07F 7/08; C07F 7/18
[52] U.S. Cl. .................... 556/419; 556/418; 556/420; 556/427; 556/429; 556/437
[58] Field of Search ............ 556/418, 419, 420, 427, 556/429, 437

[56] References Cited

U.S. PATENT DOCUMENTS

| 4,812,512 | 3/1989 | Buendia et al. ............ 556/420 X |
| 4,824,950 | 4/1989 | Barcza ..................... 556/420 X |
| 4,861,908 | 8/1989 | Satoh et al. ................ 556/420 |

FOREIGN PATENT DOCUMENTS 0935740  9/1963  United Kingdom ........... 556/418 X

Primary Examiner—Paul F. Shaver
Attorney, Agent, or Firm—Stephen V. O'Brien

[57] ABSTRACT

Compounds of formula I

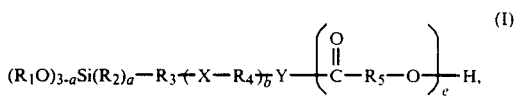

wherein
- $R_1$ is $C_1$–$C_4$alkyl, phenyl or benzyl,
- $R_2$ is $C_1$–$C_4$alkyl, phenyl or benzyl,
- a is 0, 1 or 2,
- $R_3$ is linear or branched unsubstituted or OH-substituted $C_1$–$C_{12}$alkylene or is phenylene,
- X is —O—, —X— or —NR$_6$, wherein $R_6$ is H, $C_1$–$C_4$alkyl or —CO—R$_5$—OH,
- b is 0, or
- b is an integer from 1 to 6 and $R_4$ is linear or branched unsubstituted or OH-substituted $C_1$–$C_{12}$alkylene,
- Y is —O—, —S— or —NR$_7$, wherein $R_7$ is H or $C_1$–$C_4$alkyl,
- $R_5$ is the divalent radical, diminished by the —CO—O group, of a lactone having a total of 4 to 7 ring members and containing at least one chiral carbon atom and corresponding predominantly to an optically active enantiomeric form, and e is an integer from 1 to 10.

These compounds are suitable for the preparation of stationary phases for the chromatographic separation of chiral compounds.

18 Claims, No Drawings

ENANTIOMERIC SILANES, MODIFIED PACKING MATERIAL, AND USE THEREOF

The present invention relates to enantiomers of functional organosilanes and chiral lactones, to a packing material modified with said silanes as stationary phase for chromatographic separation methods, and to the use of said packing material for the chromatographic separation of, in particular, chiral compounds.

It is known that chiral substances have different effects on an organism. The provision of chiral substances as reagent or intermediates for the preparation of chiral compounds has become of great importance. Besides the stereospecific synthesis of such compounds, chromotographic methods in particular are used for the separation of enantiomers. Mainly stationary phases are used for this purpose, a number of which are commercially available. Such stationary phases may be, for example, solid packing materials which are modified with chiral substances. It is also possible to use natural and synthetic polymers which contain chiral structural units. Silica gel, the OH groups of which may be chemically derivatised at the surface, can typically be used as solid packing material. Solid polymers containing functional groups which can be derivatised may also be suitable used. For the chiral differentiation of racemates, the packing materials can be derivatised, for example, with chiral compounds (q.v. R. Däppen et al., Journal of Chromatography, 373, pp. 1–20 (1986).

Reaction products of (aminoalkyl)alkoxysilanes with chiral lactones which may be used, for example, as couplers in glass-reinforced plastics are disclosed in U.S. Pat. No 4 104 296. In J. Org. Chem., Vol. 51, pp. 1641-1644, (1986), J. F. W. Keana at al. report on the use of silica gel modified with racemic N-[3-triethoxysilyl)propyl]-10-trichloro-10-hydroxy-10-methylundecanamide for solid phase syntheses.

In one of its aspects, the present invention relates to compounds of formula I

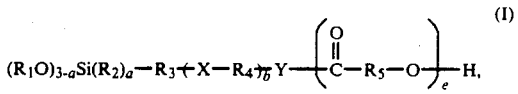

wherein
$R_1$ is $C_1$-$C_4$alkyl, phenyl or benzyl,
$R_2$ is $C_1$-$C_4$alkyl, phenyl or benzyl,
a is 0, 1 or 2,
$R_3$ is linear or branched unsubstituted or OH-substituted $C_1$-$C_{12}$alkylene or is phenylene,
X is —O—, —S— or —$NR_6$, wherein $R_6$ is H, $C_1$-$C_4$alkyl or —CO—$R_5$—OH,
b is 0, or
b is an integer from 1 to 6 and $R_4$ is a linear or branched unsubstituted or OH-substituted $C_1$-$C_{12}$alkylene,
Y is —O—, —S— or —$NR_7$, wherein $R_7$ is H or $C_1$-$C_4$alkyl,
$R_5$ is the divalent radical, diminished by the —CO—O group, of a lactone having a total of 4 to 7 ring members and containing at least one chiral carbon atom and corresponding predominantly to an optically active enantiomeric form, and e is an integer from 1 to 10.

$R_1$ as alkyl may be linear or branched and is typically methyl, ethyl, n-propyl, isopropyl, n-butyl, isobutyl or tert-butyl. The preferred meaning of $R_1$ is methyl or ethyl.

$R_2$ as alkyl may be linear or branched and is typically methyl, ethyl, n-propyl, isopropyl, n-butyl, isobutyl or tert-butyl. The preferred meaning of $R_2$ is methyl.

In formula I, a is preferably 0 or 1 and, most preferably, is 0.

$R_3$ is alkylene preferably contains 1 to 6, most preferably 3 or 4, carbon atoms, and is unsubstituted or substituted by hydroxyl. Alkylene is in particular hydroxyl-substituted if Y is —O—. Illustrative of alkylene are methylene, 1,1- or 1,2-ethylene, 1,1-, 1,2- or 1,3-propylene, 1,2-, 1,3- or 1,4-butylene, 2-methylene-1,3-propylene, 1,2-, 1,3-, 1,4- or 1,5-pentylene, 1,2-, 1,3-, 1,4-, 1,5- or 1,6-hexylene, heptylene, octylene, nonylene, decylene, undecylene or dodecylene.

$R_3$ as phenylene is preferably 1,3- or 1,4-phenylene.

More particularly $R_3$ is —$(CH_2)_n$— or —$CH_2$—$CH(CH_3)$—$CH_2$—, where n is an integer from 1 to 6, preferably 3 or 4. Most preferably, $R_3$ is 1,3-propylene.

In formula I, b may be an integer form 1 to 4 and is preferably 1 or 2.

X is preferably —O— or —$NR_5$, most preferably —$NR_6$, wherein $R_6$ is H, $C_1$-$C_4$alkyl or —CO—$R_5$—OH. Alkyl may be methyl, ethyl, n-propyl or isopropyl, n-butyl, isobutyl or tert-butyl, and is preferably methyl. Most preferably $R_6$ is H or —CO—$R_5$—OH.

$R_6$ as alkylene may independently have the meanings given for $R_3$, including the preferred meanings. Most preferably, $R_4$ is 1,2-ethylene. A preferred embodiment of the invention is that wherein X is —O— or —$NR_6$, b is an integer from 1 to 4, $R_6$ is H or —CO—$R_5$—OH, and $R_4$ is $C_1$-$C_4$alkylene. Particularly preferred compounds are those wherein b is 1 or 2, X is —$NR_6$ and $R_6$ is H or —CO—$R_5$—OH, and $R_4$ is —$CH_2CH_2$— or —$CH_2CH_2CH_2$—.

Y is preferably —O— or —$NR_7$, most preferably —$NR_7$. $R_7$ as alkyl may be methyl, ethyl, n-propyl or isopropyl, n-butyl, isobutyl or tert-butyl, methyl being particularly preferred.

A preferred subgroup of compounds of formula I comprise those compounds of formula I wherein Y is —C— or —$NR_7$ and $R_7$ is H, methyl or ethyl. Most preferably Y is —NH—.

The group —$R_3$—$(X$—$R_4)_b$—Y— in formula I is preferably —$(CH_2)_3$—NH— or —$(CH_2)_3$—$NR_6$—$CH_2CH_2$—CH—, wherein $R_6$ is H or —CO—$R_5$—OH.

In formula I e is preferably an integer from 1 to 6, more particularly from 1 to 4 and, and is most preferably 1.

Where $R_5$ is the divalent radical of a lactone, said lactone preferably contains 4 to 6, most preferably 4 or 5, ring members. Depending on the size of the ring, the lactone may contain 1 to 6, preferably 1 to 4 and, most preferably, 1 or 2, chiral carbon atoms. A chiral carbon atom in the radical $R_5$ is preferably α- or β-oriented to the OH group. The expression "predominantly optically active enantiomeric form" means, for example, not less than 90%, preferably not less than 95%, of an optically active enantiomeric form. The pure optically active enantiomeric form is preferred.

The lactones from which the divalent radical $R_5$ is derived may be, for example, at least monosubstituted lactones of saturated $C_3$-$C_6$hydroxycarboxylic acids or ethylenically unsaturated $C_4$14 $C_6$hydroxycarbonylic acids, or may be hydroxycarbonxylic acids of formula VII

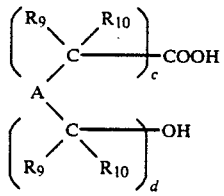

wherein c and d are each 0 or 1 and one of c or d is 1, $R_9$ and $R_{10}$ are H, $C_1$-$C_6$alkyl, —$CF_3$, or phenyl or naphthyl or substituted phenyl or naphthyl, and A is a monocyclic or polycyclic saturated or ethylenically unsaturated cycloaliphatic or heterocyclic-aliphatic radical of 4 to 18, preferably 5 to 12, carbon atoms and containing preferably O, S or N as hetero atoms, or A is $C_6$-$C_{16}$arylene in 1,2-position or $C_5$-$C_{16}$heteroarylene containing preferably O, S or N as hetero atom, with the proviso that at least one of c or d is 1 and $R_9$ and $R_{10}$ are different from each other.

These lactones or the radical A in formula VII from which $R_5$ is derived may be unsubstituted or substituted by $C_1$-$C_6$alkyl, $C_1$-$C_6$alkoxy, $C_1$-$C_6$alkylthio, $C_1$-$C_{12}$alkylamino, $C_5$ or $C_6$cycloalkyl, $C_5$ or $C_6$cycloalkoxy, $C_6$-$C_{10}$aryl, $C_6$-$C_{10}$aryloxy, $C_7$-$C_{11}$aralkyl, $C_7$-$C_{12}$aralkoxy, $C_1$-$C_6$haloalkyl, $C_1$-$C_6$hydroxyalkyl, $C_1$-$C_6$alkoxymethyl, ($C_6$-$C_{12}$aryloxy)methyl, ($C_6$-$C_{12}$acyloxy, —CO—$R_8$, —F, —Cl, —Br, —OH or —CH, where $R_8$ is $C_1$-$C_6$alkyl, cyclohexyl, phenyl or benzyl. Typical substituents are methyl, ethyl, n-propyl, isopropyl, n-butyl, isobutyl and tert-butyl, pentyl, hexyl and corresponding oxy and thio radicals; cyclopentyl, cyclohexyl and corresponding oxy and thio radicals; phenyl, phenoxy, phenylthio; benzyl, triphenylmethoxy, benzyloxy, benzylthio, fluoromethyl, trifluoromethyl, chloromethyl, trichloromethyl, β-chloroethyl; hydroxymethyl, β-hydroxyethyl; methoxymethyl, ethoxymethyl, β-methoxyethyl; phenoxymethyl, naphthoxymethyl; benzyloxymethyl, (diphenylmethoxy)methyl, (triphenylmethoxy)methyl; formyloxy, acetoxy, n-propionyloxy and isopropionyloxy, n-butyroyloxy, isobutyroyloxy and tert-butyroyloxy; —F, —Cl, —Br, —OH and —CH.

Illustrative of divalent radicals of hydroxycarboxylic acids are 1,2-propylene, 3-chloro-1,2-propylene,3,3-dichloro-1,2-propylene,3,3,3-trichloro-1,2-propylene, 3,3,3-trichloro-2-methyl-1,2-propylene,4,4,4-trichloro-1,3-butylene, but 1-enyl-1,3-ene, 2-methylbut-1-enyl-1,4-ene,1,2,3,4-tetrahydroxybutyl-1,4-ene, 1,2,3,4,5-pentahydroxypentyl-1,5-ene, 2-methyl-1,3-propylene, 2,2-dimethyl-3-hydroxy-1,3-propylene, 1-hydroxy-1,3-propylene, 1-(ethoxycarbonyl)-1,3-propylene, 1-(triphenylmethoxy)-1,3-propane, 3-(α,β-dihydroxyethyl)-1,2-dihydroxy-1,3-propylene.

The cylic non-aromatic radicals A in formula VII may be in 1,2-, 1,3- or 1,4-position. Illustrative of radicals A are 1,2-cyclobutylene, 1,2-cyclopentylene, 1,2-cyclohexylene, 2,3-tetrahydrofuranylene, cyclohex-4-enyl-1,2-ene, 1,2-phenylene, 4-nitro-1,2-phenylene, 3,5-dinitro-1,2-henylene, 2,3-naphthylene, 7-nitro-2,3-naphthylene, 2,3-pyridinylene, 2,3-furanylene, 2,3-pyrrolydene.

$R_9$ is preferably H. $R_9$ and $R_{10}$ as alkyl may be typically methyl, ethyl, n-propyl or isopropyl, n-butyl, isobutyl or tert-butyl, pentyl, hexyl, and are preferably methyl or ethyl.

Preferred compounds of formula I are those where $R_5$ is linear $C_2$-$C_5$alkylene or $C_3$-$C_5$alkenylene each of which is substituted by $C_1$-$C_6$alkyl, $C_1$-$C_6$alkoxy, $C_1$-$C_6$alkylthio, $C_1$-$C_{12}$alkylamino, $C_5$ or $C_6$cycloalkyl, $C_5$ or $C_6$cycloalkoxy, $C_6$-$C_{10}$aryl, $C_6$14 $C_{10}$aryloxy, $C_7$-$C_{11}$aralkyl, $C_7$-$C_{12}$aralkoxy, $C_1$-$C_6$haloalkyl, $C_1$-$C_6$hydroxyalkyl, $C_1$-$C_6$alkoxymethyl, ($C_6$-$C_{12}$aryloxy)methyl, ($C_6$-$C_{18}$aryl)methoxymethyl, $C_1$-$C_{12}$acyloxy, —CO—$R_8$—F, —Cl, —Br, —OH or —CN, where $R_8$ is $C_1$-$C_6$alkyl, cyclohexyl, phenyl or benzyl.

Preferred substituents are $C_1$-$C_4$alkyl, $C_1$-$C_4$alkoxy, $C_1$-$C_6$alkylamino, $C_5$ or $C_6$cycloalkyl, $C_5$ or $C_6$cycloalkoxy, phenyl, naphthyl, phenoxy, benzyl, benzyloxy, diphenylmethoxy, trityloxy, $C_1$-$C_4$haloalkyl, preferably trichloromethyl, $C_1$-$C_6$hydroxyalkyl, $C_1$-$C_4$alkoxymethyl, phenoxymethyl, benzyloxymethyl, $C_2$-$C_8$acyloxy, —CO—$OR_8$, —F, —Cl, —Br, —OH, and —CN, where $R_8$ is $C_1$-$C_4$alkyl, cyclohexyl, phenyl or benzyl.

Another preferred embodiment of this invention relates to compounds of formula I, wherein $R_5$ is a radical of formula II

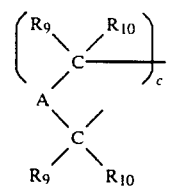

wherein

A is 1,2-phenylene or 2,3-naphthylene, each substituted or substituted by —F, —Cl, —Br, —OH, —CN, —$NO_2$, $C_1$-$C_4$alkyl or $C_1$-$C_6$alkoxy, c is 0 or 1, and $R_9$ and $R_{10}$ are different from each other and are H, $C_1$-$C_6$alkyl, —$CF_3$, unsubstituted phenyl or naphthyl, or phenyl or naphthyl each substituted by —F, —Cl, —Br, —OH, —CN, —$NO_2$, —$CF_3$, $C_1$-$C_6$alkoxy. Preferred substituents of A are —F, —Cl, —Br, —CN, —$NO_2$, $C_1$-$C_4$alkyl and $C_1$-$C_4$alkoxy.

$R_9$ and $R_{10}$ are preferably H, $C_1$-$C_4$alkyl, —$CH_3$, phenyl or naphthyl. Preferred substituents of phenyl or naphthyl are —F, —Cl, —Br, —CN, —$NO_2$, —$CH_3$, $C_1$-$C_4$alkyl or $C_1$-$C_4$alkoxy.

In a preferred embodiment of the invention, $R_5$ is the divalent radical of a β-lactone which is diminished by the —COOO group and which preferably contains one chiral carbon atom.

In a particularly preferred embodiment of the invention, $R_5$ is the R- or S-form of

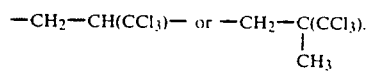

Most preferably, the compounds of formula I are the R- or S-enantiomers of formula

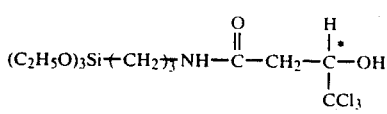

or $$(C_2H_5O)_3Si(CH_2)_3NH-\overset{O}{\underset{\|}{C}}-CH_2-\overset{CH_3}{\underset{CCl_3}{\overset{|*}{C}}}-OH$$

wherein * denotes the chiral carbon atom in R- or S-form.

The invention further relates to a process for the preparation of compounds of formula I, which comprises reacting 1 mol of a compound of formula III $$(R_1O)_{3-a}Si(R_2)_1-R_3-X-R_{4b}-Y-H \quad (III)$$

with 1 mol of a compound of formula IV $$R_5\underset{O}{\overset{\diagdown \quad \diagup}{\text{———}}}C=O \quad (IV)$$

in which formulae above $R_1$, $R_2$, $R_3$, $R_4$, $R_5$, X, Y, a, b, and e have the meanings previously assigned to them.

The method is known per se. The reaction may, for example, be carried out by adding a solution of the compound of formula III, preferably at room temperature, to a solution of lactone of formula IV. Working up can be effected by conventional methods, for example by evaporating off the solvent and purifying the distillation residue, for example by distillation, recrystallisation or chromatographic methods.

Illustrative of suitable solvents are aprotic solvents such as ethers (diethyl ether, tetrahydrofuran, dioxane), halogenated aliphatic hydrocarbons (methylene chloride, chloroform), and hydrocarbons (hexane, cyclohexane, toluene).

The compounds of formula III are known (q.v. for example U.S. Pat. Nos. 2 971 964 or 2 942 019), are obtainable by known methods or are commercially available. Very numerous optically active lactones are known or can be prepared by known methods (q.v. for example J. Chem. Soc., Vol. 104, pp. 166–168 (1982), J. Org. Chem., 52, pp. 3011–3017 (1987), J. Chromatogr., 387, pp. 313–323 (1987), Houben-Weyl 6/2, pp. 515–527 (1963), Houben-Weyl 6/2, p. 571 et seq., (1963), Houben-Weyl E 5/1, pp. 715–773 (1985), Georg Thieme Verlag, Stuttgart/New York). Racemates can be separated by known methods.

The compounds of formula I are suitable, for example, for the preparation of packing materials for chromatographic separation methods.

In another of its aspects, the present invention also relates to a packing material wherein radials of formulae Va, Vb and/or Vc $$-Si(OR_1)_{2-x}(R_2)_x-R_3(X-R_4)_bY-\left(\overset{O}{\underset{\|}{C}}-R_5-O\right)_e H \quad (Va)$$

$$\underset{\diagup}{\overset{\diagdown}{\text{Si}}}(OR_1)_{1-y}(R_2)_y-R_3(X-R_4)_bY-\left(\overset{O}{\underset{\|}{C}}-R_5-O\right)_e H \quad (Vb)$$

$$\underset{\diagup}{\overset{\diagdown}{\text{Si}}}-R_3(X-R_4)_bY-\left(\overset{O}{\underset{\|}{C}}-R_5-O\right)_e H \quad (Vc)$$

wherein x is 0,1 or 2 and y is 0 or 1, and $R_1$, $R_2$, $R_3$, $R_4R_5$, X, Y, b and e have the meanings previously assigned to them, are attached to a linking group of a solid support. The preferred meanings or $R_1$, $R_2$, $R_3$, $R_4$, $R_5$, X, Y, e and b are also as previously stated. The linking group is preferably —O—.

In yet another of its aspects, the present invention relates to a process for the preparation of a packing material, which comprises reacting
(a) a solid packing material contains radicals of formulae VIa, VIb and/or VIc $$-Si(OR_1)_{2-x}(R_2)_x-R_3(X-R_4)_bY-H \quad (VIa)$$

$$\underset{\diagup}{\overset{\diagdown}{\text{Si}}}(OR_1)_{1-y}(R_2)_y-R_3(X-R_4)_bY-H \quad (VIb)$$

$$\underset{\diagup}{\overset{\diagdown}{\text{Si}}}-R_3(X-R_4)_bY-H \quad (VIc)$$

attached through linking groups, with e mol of a lactone of formula IV $$R_5\underset{O}{\overset{\diagdown \quad \diagup}{\text{———}}}C=O \quad (IV)$$

or
(b) reacting a solid packing material which contains groups which are reactive to the silane group $(R_1O)_{3-a}Si(R_2)_a-$, with a compound of formula I, wherein x is 0, 1 or 2, and y is 0 or 1, and $R_1$, $R_2R_3$, $R_4$, $R_5$, X, Y, b and e have the meanings previously assigned to them.

The preferred meanings of $R_1$, $R_2R_3$, $R_4$, $R_5$, X, Y, b, e and x and y are also as previously stated.

The solid packing materials may be typically glass, silicates, silica gel, $Al_2O_3$ or $TiO_2$. The packing material is preferably in the form of fine particles. Such packing materials are widely described in the literature [q.v. M Verzele et al., Preparative High Performance Liquid Chromatography, Drukkerig De Muyter, Belgium, pp. 77–89 (1986); R. W. Souter, Chromatographic Separations of Stereoisomers, CRC Press, pp. 117–195 (1985), W. Noll, Chemie und Technologie der Silicone, Verlag Chemie, Weinheim (1968), Laborbücher Chemie, Praxis der Hochleistungs-Flüssigchromoatographie, Verlag Moritz Diesterweg, pp. 76–78 (1986)]. A particularly preferred packing material is silica gel.

Some of the packing materials suitable for use in process in variant (a) are commercially available or they can be prepared by known methods.

The process can be performed by carrying out the reaction in a separate reactor, and then packing a chromatography column with the reaction product. However, it is also possible to perform the process by carrying the reaction, for example, in a chromatography column or with coated thin-layer plates which are filled or coated with a packing material according to process variant (a) or (b). These processes are known per se. Process variant (a) is especially preferred.

The reaction may be carried out, for example, by suspending the packing material in an inert solvent, for example in a hydrocarbon such as hexane, benzene, toluene or xylene. To this suspension can then be added a solution of a pure enantiomeric lactone of formula IV or a compound of formula I. The solvent used for preparing the suspension will conveniently be used as solvent. During the addition, the temperature will conveniently be kept at room temperature. The reaction mixture is then further stirred, preferably at elevated temperature, for example in the range from 50° to 150° C. The reaction product can then either be packed into columns for chromatographic separations or the material is collected by filtration, washed, dried and stored for use.

The packing material of this invention is excellently suitable for use as stationary phase for the chromatographic separation of chiral compounds, especially in liquid chromatography. The invention also relates to this utility.

The chromatographic packing material of this invention affords various advantages. In process variant (a), it is obtainable in a single step reaction without auxiliary (catalyst), so that virtually no by-products are formed and high loading yields are obtained. The reaction can be carried out in packed chromatography columns. The elution sequence can be influenced by the choice of (R)- and (S)- enantiomers of the lactones. The packing material is suitable for separating racemates which are otherwise difficult to separate or which can only be separated after prior derivitisation, for example racemic diols, diamines, heterocycles and rotation isomers. Besides enantiomers, it is also possible to separate diastereoisomers and other stereoisomers. The material has high chemical stability, thereby ensuring long use. The preparative capacity is high.

The solvents employed are normally hexane, lower alcohols or ethers or mixtures thereof. The packing material of this invention makes it possible to use technical solvents and strongly polar solvent, for example $CH_2Cl_2$, $CHCl_3$, acetone, ethyl acetate, tetrahydrofuran, dioxan or acetonitrile. The use of polar solvents makes it possible to shorten the elution times substantially—a feature which is important for preparative chromatography. Supercritical solvents can also be used, for example carbon dioxide.

The high enantioselectivities are particularly surprising when in —$R_5$—OH the chiral selector

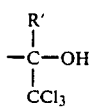

is in terminal position, where R' is H or $C_1$-$C_5$alkyl such as methyl, ethyl, propyl or butyl.

The following Examples illustrate the invention in more detail.

(A) Preparation of the starting materials

EXAMPLE 1

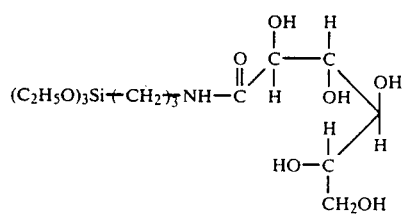

In a 250 ml three-necked flask fitted with magnetic stirrer, internal thermometer and nitrogen inlet, a solution of 11.52 g (0.05 mol) of 3-aminopropyltriethoxysilane in 25 ml of dry tetrahydrofuran (THF) is added dropwise over 20 minutes and under nitrogen to a suspension of 9.0 g (0.05 mol) of D(+)glucono-δ-lactone in THF. After stirring for 12 hours at room temperature, a clear solution is obtained. No more unreacted lactone can be detected in the reaction mixture by thin-layer chromatography. The solution is concentrated by evaporation and the solid residue is dried under vacuum, affording 19.8 g of a white crystalline product. After recrystallisation from cyclohexane/THF (6:1) with the addition of 0.6 g of activated carbon, the optically active functional silane has a melting point of >99.5° C. (dec.). The yield is 15.1 g, corresponding to 75.6% of theory.

Elemental analysis: theory 45.1% C; 8.3% H; 3.5% N; 7.0% Si found 44.8% C; 8.1% H; 3.9% N; 6.8% Si.

EXAMPLES 2-8

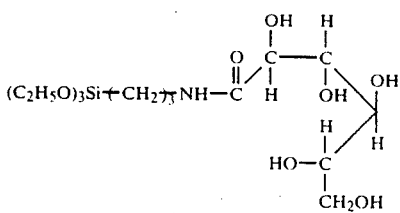

As described in Example 1, the following optically active lactones listed in Table 1 are reacted with 3-aminopropyl triethoxysilane (APTES).

TABLE 1

$$(C_2H_5O)Si(CH_2)_3NH-\overset{\overset{O}{\|}}{C}-R_5-OH$$

| Example | Lactone (g) | APTES (g) | Solvent (ml) reaction temperature (°C.) reaction time (h) | Purification | Properties | $R_5$ |
|---------|-------------|-----------|----------------------------------------------------------|--------------|------------|-------|
| 2 | $H_3C$—CH—CH$_2$, H$_2$C—C=O, O (β-methyl-β-propiolactone) (1.22 g; 0.012 mol) D-(+)-enantiomer | 2.76 g (0.012 mol) | tetrahydrofuran (25 ml) 20–30 14 | column chromatography: silica gel/ toluene | viscous colourless | $-CH_2-\overset{\overset{CH_3}{\|}}{CH}-CH_2-$ |
| 3 | $H_3C$, H, H$_3C-C-C\blacktriangleleft OH$, H$_2$C, C=O, O (1.44 g; 0.011 mol) D-(+)-enantiomer | 2.53 g (0.011 mol) | dioxane (25 ml) 20–40 12 | column chromatography: silica gel/ toluene/ tetrahydrofuran (1:1) | viscous colourless | $-\overset{\overset{H}{\|}}{C}-\overset{\overset{CH_3}{\|}}{\underset{\underset{CH_3}{\|}}{C}}-CH_2-$, OH |
| 4 | $CCl_3$, $H_3C\blacktriangleright C-CH_2$, O—C=O (4.89 g; 0.024 mol) D-(−)-enantiomer | 5.53 g (0.024 mol) | toluene (25 ml) 20–40 48 | column chromatography: silica gel/ toluene/ ethyl acetate (9:1) | viscous colourless | $-CH_2-\overset{\overset{CCl_3}{\|}}{\underset{\underset{CH_3}{\|}}{C}}-$ |
| 5 | $H_2C-CH_2$, HO CH C=O, O (1.29 g; 0.011 mol) S-(+)-enantiomer | 2.53 g (0.011 mol) | tetrahydrofuran (25 ml) 20–40 18 | recrystallisation tetrahydrofuran/diethyl ether (1:1) | white | $-CH_2-CH_2-\overset{\overset{OH}{\|}}{CH}-$ |
| 6 | $\overset{\overset{O}{\|}}{C_2H_5OC}$ $H_2C-CH_2$, CH C=O, O (1.61 g; 0.01 mol) S-(−)-enantiomer | 2.3 g (0.01 mol) | tetrahydrofuran (25 ml) 20–30 24 | column chromatography: silica gel/ ethyl acetate | viscous white | $-CH_2-CH_2-\overset{\overset{\overset{O}{\|}}{C-OC_2H_5}}{CH}-$ |
| 7 | H, $Cl_3C$ $C-CH_2$, O—C=O (4.94 g; 0.026 mol) S-(+)-enantiomer | 5.99 g (0.026 mol) | toluene (25 ml) 20–60 12 | column chromatography: silica gel/ toluene/ ethyl acetate (1:9) | viscous white | $-CH_2-\overset{\overset{CCl_3}{\|}}{\underset{\underset{H}{\|}}{C}}-$ |

TABLE 1-continued $$(C_2H_5O)Si(CH_2)_3NH-\overset{O}{\underset{\|}{C}}-R_5-OH$$

| Example | Lactone (g) | APTES (g) | Solvent (ml) reaction temperature (°C.) reaction time (h) | Purification | Properties | $R_5$ |
|---|---|---|---|---|---|---|
| 8 | 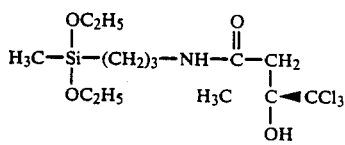<br>R = $(C_6H_5)_3C-$<br>(2.5 g; 0.0069 mol)<br>R-(−)-enantiomer | 1.52 g (0.0069 mol) | tetrahydrofuran (25 ml) 90–100 16 | column chromatography: silica gel/ toluene/ ethyl acetate (1:9) | viscous colourless | $\begin{array}{c}CH_2OR\\ |\\ -CH_2-CH_2-CH-\end{array}$ |

EXAMPLE 9

$$\begin{array}{c}OC_2H_5\quad\quad O\\ |\quad\quad\quad\quad\|\\ H_3C-Si-(CH_2)_3-NH-C-CH_2\\ |\quad\quad\quad\quad\quad |\\ OC_2H_5\quad\quad H_3C-C-CCl_3\\ \quad\quad\quad\quad\quad\quad |\\ \quad\quad\quad\quad\quad\quad OH\end{array}$$

In accordance with Example 1, a solution of 4.78 g (0.025 mol) of 3-aminopropylmethyl diethoxysilane in 10 ml of dry toluene is added dropwise at room temperature to a solution of 5.09 g (0.025 mol) of R-(+)-4-methyl-4-trichormethyl-2-oxetanone in 20 ml of dry toluene, while cooling with water such that the temperature does not exceed 40° C. The reaction mixture is then stirred for 12 hours at room temperature. After removal of the solvent by evaporation the highly viscous residue (9.5 g) is purified by column chromatography over silica gel with hexane/diethyl ether (9:1) as eluant, affording 8.4 g (85% of theory) of a colourless viscous product.

Elemetnal analysis: theory: 39.55% C; 6.64% H; 3.55% N; 26.94% Cl; 7.11% Si. found: 39.7% C; 6.8% H; 3.5% N; 26.7% Cl; 7.4% Si.

EXAMPLE 10

With moderate stirring, a solution of 10.4 g (0.055 mol) of R(−)-4-trichloromethyl)-2-oxetanone (Lonza AG, Basel) in 25 ml of dry toluene is added dropwise at room temperature over 30 minutes to a suspension of 56 g of dry aminopropylated silica gel (LiChroprep NH$_2$, Merck AG, Darmstadt; particle size 25–40 μm, N-content 1.36%, corresponding to 0.97 mVal/g of silica gel) in 25 ml of dry toluene. The mixture is stirred for 12 hours at room temperature and then for 7 hours at 70° C., while monitoring the consumption of oxetanone by gas chromatography. After consumption of the oxetanone, the modified silica gel is filtered through a G4 glass frit, washed with three 200 ml portions of dry toluene, and finally dried in a high vacuum at 0.133 pa.s/20°–60° C., to give 63.9 (96.3% of theory) of a chirally modified packing material whose particle size distribution, specific surface are and pore size distribution is virtually unchanged in comparison with the starting material. The product contains 8.24% of chlorine and 1.24% of nitrogen, corresponding to a content of 0.775 mmol/g of chiral (R)-4,4-trichloro-3-hydroxybutyramide groups and an 80% conversion of the amino groups originally present.

EXAMPLE 11

In accordance with Example 10, 5 g of dry aminopropylated silicagel (LiChrosorb NH$_2$, Merck AG, Darmstadt; particle size 5 μm, N-content 1.36%, corresponding to 0.97 mVal/g of silica gel) are reacted at 20°–70° C. with 1.5 g (0.00793 mol) of (R)-4-(trichloromethyl-2-oxetanone in 70 ml of dry toluene. Yield: 5.5 g (93.0% of theory) of a chirally modified finely particulate silica gel which contains 1.24% of nitrogen and 7.53% of chlorine, corresponding to a content of 0.708 mmol/g of (R)-4,4,4-trichloro-3-hydroxybutyramide groups and a 73% conversion of the amino groups bonded to silica gel.

EXAMPLE 12

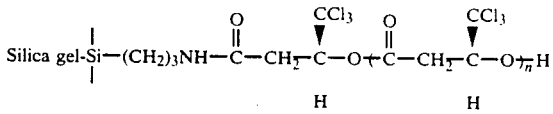

In accordance with Example 10, 8 g of aminopropylated silica gel (N-content: 1.04 mVal/g; particle size 10 μm) in 80 ml of dry tetrahydrofuran are reacted at 20°–60° C. for 40 hours, under nitrogen, with 15.8 g (0.0832 mol) of R(−)-4-(trichloromethyl)-2-oxetanone, with the addition of 4 drops of dibutyltin dilaurate. Yield: 8.9 g of a chirally modified silica gel with a nitrogen content of 1.4% and a chlorine content of 9.3%, equivalent to a chiral group content of 0.874 mmol/g.

EXAMPLE 13

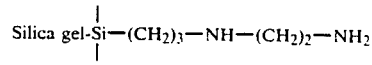

A suspension of 500 g of silica gel (silica gel Si 60, Merck AG, Darmstadt; particle size 15–25 μm) in 3 liters of toluene is freed from water by azeotropic distillation in a water separator. Then 500 g of 3-[N-2-aminoethyl)]aminopropyltrimethoxysilane are added, and the methanol formed during the reaction is removed by distillation through a 50 cm packed column. After 10 hours, no more freshly formed methanol can be detected in the distillate by gas chromatography. The modified silica gel is isolated by filtration through a glass frit, washed with three 300 ml portions of dry toluene, and dried to constant weight in a high vacuum, affording 630 g of product. Elemental analysis shows a content of 8.0% C, 2.1% H and 3.6% N. These values correspond to a content of 1.28 mmol of 3-[N-(2-aminotheyl)]aminopropyl groups per g of modified silica gel.

EXAMPLES 14–18

In accordance with Example 13, the silica gels listed in Table 2 are reacted with silanes
APTES = 3-aminopropyltriethoxysilane (Fluka AG, Buchs)
GF 91 = 3-[N-(2-aminoethyl)]aminopropyltrimethoxysilane (Wacker AG, Burghausen, FRG).

65.33 g (88% of theory) of chirally modified silica gel are obtained. Elemental analysis gives the following values: 12.12% C, 1.85% H, 2.57% N and 13.98% Cl. From the elemental analysis it is possible to determine that the material contains 1.31 mmol of (R)-4,4,4-trichloro-3-hydroxybutyramide groups per g, corresponding to a conversion of 51.2%, based on the total amount of primary and secondary amino groups in the starting material. The chirally modified silica gel so obtained has a specific surface area (BET) of 163 m$^2$/g and a mean particle size distribution of 19 μm, indicating that the porous particulate structure of the silica gel is not adversely influenced by the treatment.

EXAMPLES 20–24

TABLE 2

| Ex. | Silica gel amount | Solvent | Aminosilane amount | Amount of product and functionality | Properties |
|---|---|---|---|---|---|
| 14 | Matrex Silica medium (5 μm; 100 Å) (Amicon Corp., Lausanne) 24.2 g | toluene (250 ml) | GF-91 (24.2 g) | 28.2 g and 1.03 mmol/g | elemental analysis: 6.7% C 1.7% H 2.9% N spec. surface area (BET): 225 m$^2$/g |
| 15 | Aerosil 380 (7 nm; 380 m$^2$/g) (Degussa, Frankfurt) (75 g) | toluene (2000 ml) | APTES (112.5 g) | 84.7 g and 1.35 mmol/g | elemental analysis: 6.4% C 1.6% H 1.9% N spec. surface area (BET): 189 m$^2$/g |
| 16 | Aerosil 200 (12 nm; 200 m$^2$/g) (Degussa, Frankfurt) (70 g) | toluene (2000 ml) | APTES (105 g) | 78.1 g and 2.0 mmol/g | elemental analysis: 8.0% C 1.9% H 2.8% N spec. surface area (BET): 125 m$^2$/g |
| 17 | Aerosil 380 (7 nm; 380 m$^2$/g) (Degussa, Frankfurt) (68 g) | toluene (2000 ml) | GF-91 (107 g) | 77.7 g and 1.57 mmol/g | elemental analysis: 8.3% C 2.0% H 4.4% N spec. surface area (BET): 156 m$^2$/g |
| 18 | Aerosil 200 (12 nm; 200 m$^2$/g) (Degussa, Frankfurt) (80.5 g) | toluene (2000 ml) | GF-91 (127 g) | 87.3 g and 1.0 mmol/g | elemental analysis: 6.2% C 1.5% H 2.8% N spec. surface area (BET): 129 m$^2$/g |

*Examples 15 and 16 based on mmol of —(CH$_2$)$_3$—NH$_2$
Examples 14, 17 and 18 based on mmol of —(CH$_2$)$_3$—NH—(CH$_2$)$_2$—NH$_2$

EXAMPLE 19

As described in Example 10, 50 g of the modified silica gel prepared in Example 13 are reacted with 36.5 g (0.19 mol) of R-(−)-4-trichloromethyl-2-oxetanone in 250 ml of toluene. After filtration, washing and drying, As indicated in the following Table 3, further amino group containing silica gels and organic polymer materials are reacted with a number of optically active lactones in accordance with the reaction conditions of Example 19.

TABLE 3

| Ex. | Amino group containing material (amount) | Chiral lactone (amount) | Solvent (amount) | Amount of product and functionality* | Properties |
|---|---|---|---|---|---|
| 20 | Silica gel prepared according to Example 14 (15 g) | 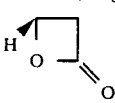 (7.2 g) S(+)-form | toluene (75 ml) | 18.3 g and 1.23 mmol/g | 10.9% C 1.7% H 2.3% N 13.1% Cl |

TABLE 3-continued

| Ex. | Amino group containing material (amount) | Chiral lactone (amount) | Solvent (amount) | Amount of product and functionality* | Properties |
|---|---|---|---|---|---|
| 21 | amino-functionalised Aerosil according to Example 15 (5 g) | 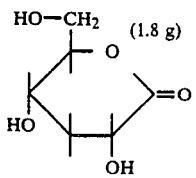 (1.8 g) D(+)-form | N,N-dimethyl-acetamide (90 ml) | 5.8 g and 0.46 mmol/g | 9.2% C 1.9% H 1.2% N |
| 22 | amino-functionalised Aerosil according to Example 16 (5 g) | 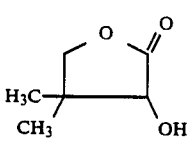 (2 g) D(−)-form | dioxane (75 ml) | 6.5 g and 0.34 mmol/g | 13.6% C 1.9% H 2.1% N |
| 23 | amino-functionalised Aerosil according to Example 17 (3.5 g) | 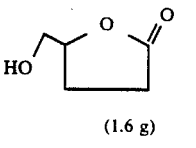 (1.6 g) S(+)-form | dioxane (60 ml) | 4.3 g and 0.37 mmol/g | 12.7% C 2.3% H 3.1% N |
| 24 | amino-functionalised Aerosil according to Example 18 (5 g) | 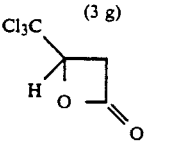 (3 g) R(+)-form | dioxane (70 ml) | 7.1 g and 0.69 mmol/g | 9.1% C 1.5% H 2.3% N 7.3% Cl |

*based on grafted hydroxycarboxylic acid radicals

EXAMPLE 25

Chiral modification of TLC plates:

Aminopropylated silica gel plates for thin-layer chromatography (HPTLC plate $NH_2F_{254}S$, Merck AG, Darmstadt) are immersed for 48 hours at room temperature in a solution of 20 g of R-(−)-4-trichloromethyl-2-oxetanone in 400 ml of dry toluene. After this treatment, the plates are freed from unreacted lactone by washing 3 times over 24 hours with fresh toluene and then drying them to constant weight under $N_2$ at 40° C./0.133 Pa.s. The elemental analysis of the coated plates so obtained in comparison with that of the starting plates is as follows:

| | | | | |
|---|---|---|---|---|
| HPTLC plates $NH_2F_{254}S$: | 6.2% C | 2.2% H | 2.0% N | >0.3% Cl |
| lactone-treated plates: | 9.0% C | 1.9% H | 1.9% N | 7.4% Cl. |

The result corresponds to a loading of the coated material with 0.696 mmol/g of chiral R(−)-4-trichloromethyl-3-hydroxybutyramide groups.

With the aid of the new TLC plates it is possible, for example, to separate and identify the enantiomers of racemic 2,2′-dihydroxy-1,1′-binaphthyl. Using chloroform as eluant, the (−)-enantiomer has an Rf value of 0.88 and the (+)-enantiomer an Rf value of 0.83.

EXAMPLES 26-33

In situ treatment of amino-functionalised HPLC silica gel columns with optically active lactones Commercially available steel columns which are obtainable from a variety of manufacturers are used for the chiral modification of ready-packed amino-functionalised HPLC silica gel columns. Additionally, commercially available aminoalkylated silica gel columns or the silica gels described in Examples 13-18 using the slurry technique in conventional manner as described, for example, by C. C. Siemon, J. Liquid Chromatogr. 6, 765 (1983), can be used for packing the HPLC columns.

The chemical modification of the amino-functionalised HPLC column systems so obtained is effected by pumping a 2–10% solution of the appropriate optically active lactone in a solvent such as methanol, isopropanol, tetrahydrofuran, methylene chloride or hexane, at a temperature of 20–40° C. over 10–72 hours, through the respective column. The consumption of lactones is monitored by UV spectrometry or by gas chromatography or by refraction measurement. When the reaction is complete, the column is repeatedly washed with pure solvent, and finally the amount of unconsumed lactone is determined gravimetrically by evaporating the combined reaction and washing solutions.

The theoretical number of plates of the columns, as benchmark for assessing the quality of the packing, is determined in conventional manner with toluene as reference substance as described, for example, by V.

Meyer, "Praxis der Hochleistungsflüssigchromatographie", 4th edition, Diesterweg/Salle/Sauerländer 1986, page 20, Frankfurt. The reaction conditions and results are summarised in Table 4.

attenuation: 8

Characterisation is effected in conventional manner, for example as described in V. Meyer, "Praxis der Hochleistungsflüssigchromatographie", Diesterweg/Sal-

TABLE 4

| Ex. | Amino-functionalised silica gel | Column dimensions (length × diameter) | Chiral lactone, amount, solvent | Temperature time | Amount of reacted lactone | Theoretical number of plates |
|---|---|---|---|---|---|---|
| 26 | Matrex silica (5 μm; 100 Å; 0.55 mmolNH₂/g) Amicon, Lausanne | 250 mm × 4.6 mm | R(−)-4-trichloro-methyl-2-oxetanone, 0.5 g/20 ml hexane | 25° C. 48 h | 352 mg | 10'400 |
| 27 | Nucleosil-NH₂ (10 μm; 300 Å; 0.51 mmolNH₂/g) Macherey & Nagel, Duren | 250 mm × 4.6 mm | S(+)-4-trichloro-methyl-2-oxetanone, 0.5 g/20 ml hexane/CH₂Cl₂ (80:20) | 25° C. 18 h | 314 mg | 11'130 |
| 28 | Spherisorb-NH₂ (3 μm) | 250 mm × 4.6 mm | S(+)-4-trichloro-methyl-2-oxetanone, 0.665 g/30 ml hexane/isopropanol (95:5) | 20–40° C. 60 h | 497 mg | 18'820 |
| 29 | Nucleosil-NH₂ (5 μm; 100 Å) | 200 mm × 4.0 mm | 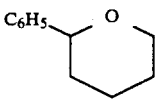 (+)-enantiomer, 0.5 g/25 ml hexane/THF (80:20) | 20–40° C. 48 h | 230 mg | 8'530 |
| 30 | LiChrosorb-NH₂ (7 μm) | 250 mm × 25 mm | R(−)-4-trichloro-methyl-2-oxetanone, 15 g/600 ml hexane/CH₂Cl₂ (80:20) | 20–30° C. 72 h | 7.8 mg | 10'060 |
| 31 | LiChrosorb-NH₂ (10 μm) | 250 mm × 50 mm | S(+)-4-trichloro-methyl-2-oxetanone, 60 g/2.5 l hexane/CH₂Cl₂ (80:20) | 20–40° C. 72 h | 43 mg | 10'800 |
| 32 | Nucleosil-NH₂ (10 μm) | 250 mm × 4.6 mm | R(+)-4-trichloro-methyl-2-oxetanone, 0.53 g/30 ml hexane/CH₂Cl₂ (80:20) | 20–40° C. 48 h | 380 mg | 9'200 |
| 33 | Example 28 | 250 mm × 4.6 mm | S(+)-4-trichloro-methyl-2-oxetanone | 25° C. 48 h | 450 mg | 14'000 |

EXAMPLE 34

In a slight modification of the conventional technique for packing HPLC analytical columns, the chirally modified silica gel described in Example 11 is used for packing a steel column with a length of 250 mm and an internal diameter of 4.6 mm. The procedure comprises suspending 3.5 g of the silica gel in 55 ml of a mixture of hexane/isopropanol (95:5) and ultrasonicating the suspension for 3 minutes. After transferring the suspension to a steel vessel equipped with magnetic stirrer and on to the cover of which the steel column to be packed in screwed, the suspension is passed through a packing in the column under a pressure of 250 bar and a rate of flow of 10 ml/min by the ascending technique.

The customary quality test of the packing using toluene as reference substance and eluting with hexane/isopropanol (90:10) gives a stagnant volume of 3.2 ml and a theoretical number of plates of 10 700.

(B) USE EXAMPLES

EXAMPLE 35

The chirally modified HPLC silica gel column described in Example 34 is used for the analytical separation of racemic 2,2'-dihydroxy-1,1'-binaphthyl, using a Shimadzu LC-6A HPLC system. The chromatographic parameters used are:
eluant: chloroform
UV detection: 254 nm
flow rate: 1.3 ml/min
pressure: 181.5 bar le/Sauerländer, 4th edition, Frankfurt 1986, page 18 et seq., with the capacity factors $k_1$ and $k_2$ as well as the separation factor $\alpha$ and the resolution factor $R_s$:
$k_1 = 0.39$
$k_2 = 0.63$
$\alpha = 1.61$
$R_s = 2.3$.

EXAMPLE 36

As described in Example 35, the following racemic substances

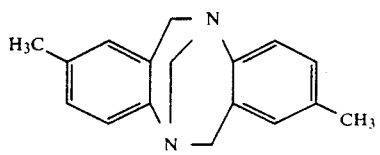

A

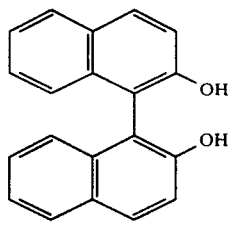

B

-continued

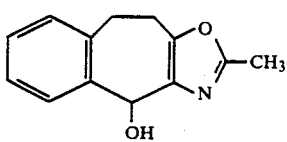

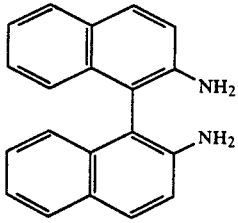

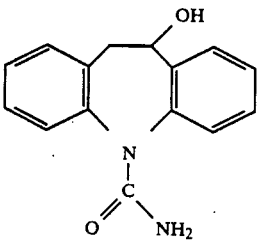

-continued

C 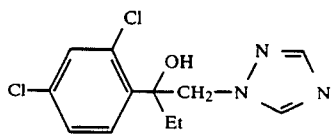   F

D 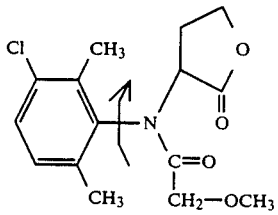   G

E  (aR, 1'S and aS, 1'R)

20 are investigated using the chiral HPLC columns described in the preceeding Examples. The chromatographic parameters used and the results are summarised in Table 5.

Supercritical CO₂ or combinations of supercritical CO₂ *with polar modifiers such as* 2-propanol can also be used as eluant.

TABLE 5

| Column of Example | Substance | Sample concentration | Eluant | Pressure [bar] flow rate [ml/min] | k₁' | k₂' | α | Rₛ |
|---|---|---|---|---|---|---|---|---|
| 34 | B | 2 μl (2.5 mg/ml) | CHCl₃ | 42 0.5 | 0.13 | 0.37 | 2.86 | 2.81 |
| 34 | A | 2 μl (5 mg/ml) | hexane/t-butyl-methyl ether (90:10) | 0 0.5 | 6.72 | 7.35 | 1.09 | 1.31 |
| 34 | C | 5 μl (5 mg/ml) | hexane/CHCl₃/acetonitrile (49:50:1) | 130 1 | 7.53 | 8.54 | 1.13 | 1.43 |
| 34 | D | 2 μl (8.8 mg/ml) | hexane/2-propanol (95:5) | 0 0.5 | 1.96 | 2.14 | 1.1 | 1.17 |
| 34 | E | 2 μl (5 mg/ml) | hexane/2-propanol (98:2) | 0 0.5 | 3.06 | 3.36 | 1.1 | 1.46 |
| 34 | F | 2 μl (7.2 mg/ml) | hexane/CHCl₃/acetonitrile (49:50:1) | 155 1 | 2.74 | 3.01 | 1.1 | 1.48 |
| 34 | G | 2 μl (6 mg/ml) | CHCl₃ | 43 1 | 1.03 | 1.12 | 1.08 | 1.21 |
| 34 | A | 1 μl (4 mg/ml) | hexane/2-propanol (90:10) | 0 0.5 | 0.75 | 1.08 | 1.44 | 1.74 |
| 26 | A | 2 μl (5 mg/ml) | hexane/2-propanol (95:5) | 0 0.5 | 1.9 | 2.71 | 1.43 | 3.63 |
| 26 | C | 2 μl (4 mg/ml) | hexane/2-propanol (95:5) | 0 0.5 | 2.4 | 2.88 | 1.20 | 2.52 |
| 26 | F | 2 μl (5 mg/ml) | hexane/2-propanol (98:2) | 0 0.5 | 4.92 | 5.44 | 1.11 | 1.68 |
| 26 | A | 2 μl (5 mg/ml) | hexane/CH₂Cl₂ (1:1) | 0 0.5 | 0.87 | 1.2 | 1.37 | 2.47 |
| 34 | A | 5 μl (1 mg/ml) | CO₂/2-propanol (90:10) | 375.8 Δp 58.60 2 | 0.44 | 0.67 | 1.53 | 2.34 |
| 34 | A | 5 μl (1 mg/ml) | CO₂/2-propanol (85:15) | 379.2 Δp 62.05 2 | 0.10 | 0.23 | 2.39 | 1.37 |
| 28 | A | 2 μl (3 mg/ml) | hexane/2-propanol (95:5) | 44 1 | 2.03 | 2.82 | 1.38 | 5.16 |
| 28 | A | 2 μl (2.5 mg/ml) | CHCl₃ | 70 1 | 0.46 | 0.73 | 1.58 | 4.74 |
| 28 | A | 4 μl (9.5 mg/ml) | CHCl₃/1,1,1-trichloroethane (4:1) | 113 1 | 0.18 | 0.31 | 1.72 | 1.72 |
| 28 | A | 2 μl (2.5 mg/ml) | CHCl₃/hexane/acetonitrile (50:49:1) | 89 1 | 1.91 | 2.58 | 1.35 | 2.99 |
| 28 | G | 2 μl (5 mg/ml) | CHCl₃/hexane/acetonitrile (50:49:1) | 56 1 | 3.79 | 4.12 | 1.09 | 1.4 |

TABLE 5-continued

| Column of Example | Substance | Sample concentration | Eluant | Pressure [bar] flow rate [ml/min] | $k_1'$ | $k_2'$ | α | $R_s$ |
|---|---|---|---|---|---|---|---|---|
| 28 | G | 2 μl (9 mg/ml) | CHCl$_3$ | 67 1 | 2.38 | 2.55 | 1.07 | 0.98 |
| 28 | G | 4 μl (8 mg/ml) | CHCl$_3$/acetonitrile (99:1) | 125 1 | 1.09 | 1.19 | 1.09 | 1.1 |
| 26 | A | 50 μl (20 mg/ml) | hexane/2-propanol (95:5) | 0 0.5 | 1.63 | 2.23 | 1.41 | 1.57 |
| 30 | A | 1000 μl (28 mg/ml) | hexane/2-propanol (95:5) | 5 9.9 | 1.0 | 1.3 | 1.29 | 1.02 |
| 31 | A | 3000 μl (20 mg/ml) | heptane/2-propanol (95:5) | 0 60 | 1.01 | 1.38 | 1.37 | 1.67 |
| 33 | C | 5 μl (1 mg/ml) | CHCl$_3$/hexane/ acetonitrile (50:49:1) | 32 1 | 1.17 | 1.38 | 1.18 | 1.64 |
| 27 | C | 5 μl (1 mg/ml) | CHCl$_3$/hexane/ acetonitrile (50:49:1) | 21 1 | 8.65 | 9.40 | 1.09 | 1.26 |
| 27* | C | 5 μl (1 mg/ml) | CHCl$_3$/hexane/ acetonitrile (50:49:1) | 21 1 | 5.08 | 6.09 | 1.20 | 2.60 |
| 34 | C | 10 μl (1 mg/ml) | CHCl$_3$/hexane/ acetonitrile (50:49:1) | 50 1 | 1.03 | 1.25 | 1.21 | 1.04 |

*Addition of 0.5% of (R)-N-hexyl-4,4,4-trichloro-3-hydroxybutyramide.

What is claimed is:

1. A compound of formula I

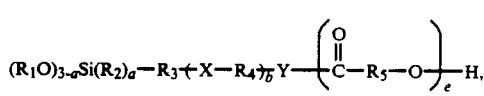

wherein
$R_1$ is $C_1-C_4$alkyl, phenyl or benzyl,
$R_2$ is $C_1-C_4$alkyl, phenyl or benzyl,
a is 0, 1 or 2,
$R_3$ is linear or branched unsubstituted or OH-substituted $C_1-C_{12}$alkylene or is phenylene,
X id —O—, —S— or —NR$_6$, wherein R$_6$ is H, $C_1-C_4$alkyl or —CO—R$_5$—OH,
b is 0, or
b is an integer from 1 to 6 and R$_4$ is linear or branched unsubstituted or OH-substituted $C_1-C_{12}$alkylene,
Y is —O—, —S— or —NR$_7$, wherein R$_7$ is H or $C_1-C_4$alkyl,
$R_5$ is the divalent radical, diminished by the —CO—O group, of a lactone having a total of 4 to 7 ring members containing at least one chiral carbon atom and corresponding predominantly to an optically active enantiomeric form, and e is an integer from 1 to 10.

2. A compound according to claim 1 wherein $R_1$ is methyl or ethyl.

3. A compound according to claim 1 wherein $R_2$ is methyl.

4. A compound according to claim 1 wherein a is 0 or 1.

5. A compound according to claim 1 wherein $R_3$ is unsubstituted or OH-substituted $C_1-C_6$alkylene or is phenylene.

6. A compound according to claim 5, wherein $R_5$ is un substituted or OH-substituted $C_3-C_4$alkylene or is 1,3- or 1,4-phenylene.

7. A compound according to claim 6, wherein $R_3$ is —(CH$_2$)$_n$—, —CH(CH$_3$)—, —CH$_2$—CH(CH$_3$)—CH$_2$—, and n is 3 or 4.

8. A compound according to claim 1, wherein X is —O— or —NR$_6$, b is an integer from 1 to 4, R$_6$ is H or —CO—R$_5$—OH, and R$_4$ is $C_1-C_4$alkylene.

9. A compound according to claim 8, wherein b is 1 or 2, X is —NR$_6$ and R$_6$ is H or —CO—R$_5$—OH, and R$_4$ is —CH$_2$CH$_2$— or —CH$_2$CH$_2$CH$_2$—.

10. A compound according to claim 1, wherein Y is —NR$_7$ and R$_7$ is H, methyl or ethyl.

11. A compound according to claim 10, wherein Y is —NH.

12. A compound according to claim 1, wherein R$_4$ is the divalent radical of a lactone containing a total of 4 or 5 ring members.

13. A compound according to claim 1, wherein R$_5$ is linear $C_2-C_5$akylene or $C_3-C_5$alkenylene, each of which is substituted by $C_1-C_6$alkyl, $C_1-C_6$alkoxy, $C_1-C_6$alkylthio, $C_1-C_{12}$alkylamino, $C_5$ or $C_6$cycloalkyl, $C_5$ or $C_6$cycloalkyl, $C_5$ or $C_6$cycloalkoxy, $C_6-C_{10}$aryl, $C_6-C_{10}$aryloxy, $C_7-C_{11}$aralkyl, $C_7-C_{12}$aralkoxy, $C_1-C_6$haloalkyl, $C_1-C_6$hydroxyalkyl, $C_1-C_6$alkoxymethyl, ($C_6-C_{12}$aryloxy)methyl, ($C_6-C_{18}$aryl)methoxymethyl, $C_1-C_{12}$acyloxy, —CO—R$_8$, —F, —Cl, —Br, —OH or —CN, where R$_8$ is $C_1-C_6$alkyl, cyclohexyl, phenyl or benzyl.

14. A compound according to claim 1, wherein R$_5$ is a radical of formula II

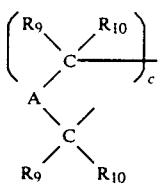

wherein
A is 1,2-phenylene or 2,3-naphthylene, each unsubstituted or substituted by —F, —Cl, —Br, —OH, —CN, —NO$_2$, $C_1-C_4$alkyl or $C_1-C_6$aloxy,
c is 0 or 1, and
R$_9$ and R$_{10}$ are different from each other and are H, $C_1-C_6$alkyl, —CH$_3$, unsubstituted phenyl or naphthyl, or phenyl or naphthyl each subsituted by —F, —Cl, —Br, —OH, —CN, —NO$_2$, —CF$_3$, C$_1$-C$_6$alkyl or C$_1$-C$_6$alkoxy.

15. A compound according to claim 1, wherein a chiral carbon atom in the radical R$_5$ is α- or β-orientated to the OH group.

16. A compound according to claim 1, wherein R$_5$ is the R- or S-form of —CH$_2$—CH(CCl$_3$)—

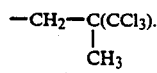

17. A compound according to claim 1, which is the R- or S-enantiomer of formula

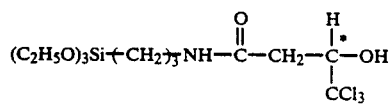

or

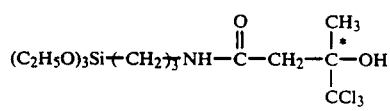

wherein * denotes the chiral carbon atom in R- or S-form.

18. A process for the preparation of a compound of formula I, which comprises reacting 1 mol of a compound of formula III

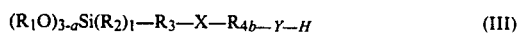

with 1 mol of a compound of formula IV

in which formulae above R$_1$, R$_2$, R$_3$, R$_4$, R$_5$, X, Y, a, b, and e are as defined in claim 1.

* * * * *